United States Patent [19]

Groger et al.

[11] Patent Number: 5,745,231
[45] Date of Patent: Apr. 28, 1998

[54] METHOD OF FLUORESCENCE ANALYSIS COMPRISING EVANESCENT WAVE EXCITATION AND OUT-OF-PLANE PHOTODETECTION

[75] Inventors: Howard P. Groger, Gainesville, Fla.; K. Peter Lo, Blacksburg, Va.; Martin Weiss, New Port Richey, Fla.

[73] Assignee: American Research Corporation of Virginia, Radford, Va.

[21] Appl. No.: 489,436

[22] Filed: Jun. 12, 1995

[51] Int. Cl.$^6$ .................... G01N 21/41; G01N 21/00
[52] U.S. Cl. .................. 356/128; 356/432; 356/436
[58] Field of Search ..................... 356/409–412, 356/440, 441, 436, 300, 39, 432–435, 73, 244, 318, 114; 422/57–58, 82.06–82.07, 82.11; 385/12, 13; 250/573–576, 227.11, 227.14

[56] References Cited

U.S. PATENT DOCUMENTS

| | | | |
|---|---|---|---|
| 4,035,082 | 7/1977 | Kirschen | 356/114 |
| 4,549,807 | 10/1985 | Hoffmaster | 356/318 |
| 4,716,121 | 12/1987 | Block et al. | 436/514 |
| 4,752,115 | 6/1988 | Murray, Jr. et al. | 350/96.29 |
| 4,775,214 | 10/1988 | Johnson | 350/96.29 |
| 4,844,613 | 7/1989 | Batchelder | 356/318 |
| 4,852,967 | 8/1989 | Cook et al. | 350/96.29 |
| 4,880,752 | 11/1989 | Keck et al. | 435/7 |
| 5,004,913 | 4/1991 | Kleinerman | 250/227.21 |
| 5,039,492 | 8/1991 | Saaski et al. | 422/82.09 |
| 5,061,857 | 10/1991 | Thompson et al. | 250/458.1 |
| 5,071,248 | 12/1991 | Tiefenthaler et al. | 356/128 |
| 5,094,517 | 3/1992 | Franke | 385/12 |
| 5,095,514 | 3/1992 | Curtis | 385/12 |
| 5,156,976 | 10/1992 | Slovacek et al. | 436/164 |
| 5,166,515 | 11/1992 | Attridge | 250/227.25 |
| 5,170,448 | 12/1992 | Ackley et al. | 385/31 |
| 5,195,162 | 3/1993 | Sultan et al. | 385/130 |
| 5,307,146 | 4/1994 | Porter | 356/320 |
| 5,315,672 | 5/1994 | Padovani | 385/12 |
| 5,340,715 | 8/1994 | Slovacek et al. | 435/6 |
| 5,344,784 | 9/1994 | Attridge | 436/518 |
| 5,489,988 | 2/1996 | Ackley | 356/436 |

*Primary Examiner*—Frank G. Font
*Assistant Examiner*—Michael P. Stafira
*Attorney, Agent, or Firm*—James Creighton Wray; Meera P. Narasimhan

[57] ABSTRACT

Fluorescence measuring methods and apparatus use planar optical waveguides to excite fluorescence in the evanescent field of the waveguides and photodetectors to sense the fluorescence produced. Chemically sensitive fluorophores are bound to the evanescent regions of the planar optical waveguides. Substrates support the waveguides. Photodetectors, positioned in the substrates with fields of view normal to the waveguides, detect the fluorescence. Wavelength-selective material coating surfaces of the photodetectors allow fluorescence to be detected while restricting entry of light at the excitation wavelengths. The photodetectors have high aspect ratios for detection of fluorescence generated by the optical waveguides. Preferably, the photodetectors are closely coupled to the fluorescence generated in the evanescent field of the waveguide. In alternative embodiments, lightguides near the waveguides direct fluorescence from the plane of the waveguides for transmission by integrated optical fibers to remote sensors. For chemical detection and analysis, energy is introduced to an edge of the waveguide. The edges are coated to reflect the energizing energy throughout the waveguide. The energy excites the chemically sensitive fluorophore film positioned on the waveguide. Inexpensive photodetectors without expensive photo-multipliers are mounted in substrates beneath the waveguides or at ends of lightguides extending from the substrates for detecting fluorescence.

18 Claims, 2 Drawing Sheets

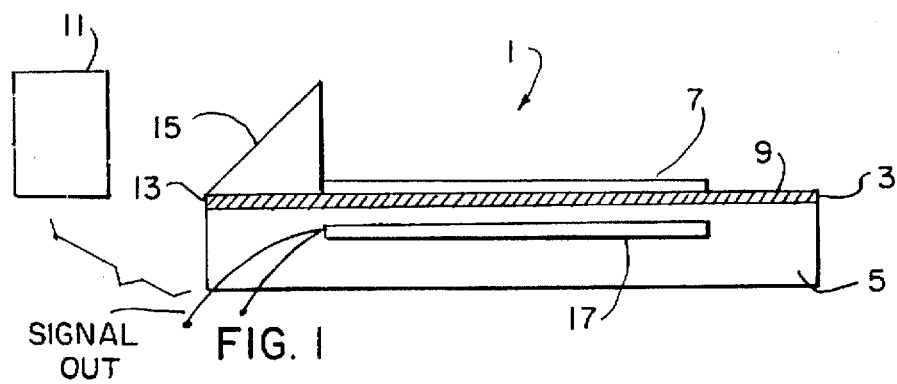
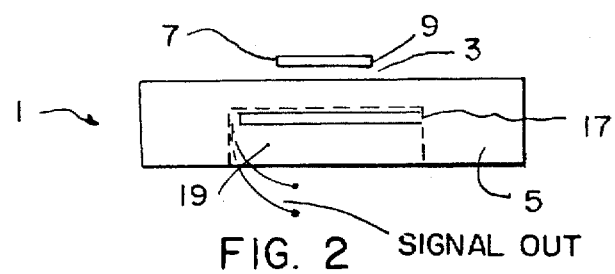
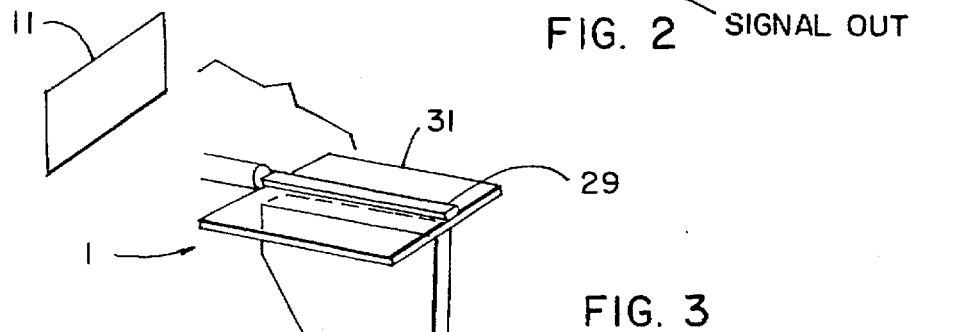
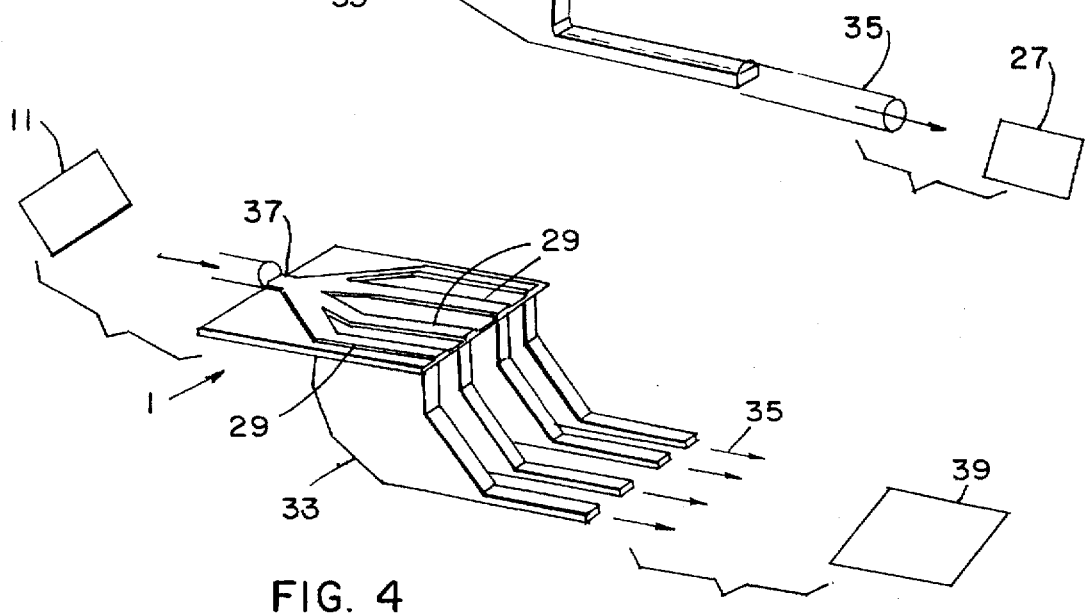

METHOD OF FLUORESCENCE ANALYSIS COMPRISING EVANESCENT WAVE EXCITATION AND OUT-OF-PLANE PHOTODETECTION

BACKGROUND OF THE INVENTION

This invention relates to fluorescence sensors for chemical detection and analysis.

Optical fluorescence sensors are useful in analyzing chemical properties of liquid and gas-phase analytes. Existing fluorescence methods and apparatus are based on evanescent wave excitation and in-plane fluorescence detection. Those methods and apparatus suffer from low efficiency of collection of fluorescent light. Effective analysis requires the use of expensive photomultiplier tubes for adequate fluorescence detection. Drift and other noise effects associated with the use of photomultiplier tube devices reduce sensor precision and result in inaccurate analysis. Needs exist for sensors that have out-of-plane detection and eliminate the need for expensive photomultiplier tubes.

Evanescent wave excitation allows monitoring chemical reactions within a short distance of the excitation beam. The sensitivity of chemical sensors based on evanescent wave excitation is limited by the amount of fluorescence coupled to the waveguide. The amount of fluorescence collected by a photodetector is limited by inefficiencies associated with coupling light from the source to the optical waveguide. Additionally, the specificity of a fluorescent sensor is reduced by interferences resulting from chemical reactions between sensor material and materials other than the analyte of interest. Needs exist for fluorescent waveguide sensors having increased specificity, sensitivity and precision.

SUMMARY OF THE INVENTION

The present invention provides a highly sensitive optical fluorescence sensor and related method that combine both evanescent wave excitation and out-of-plane detection. The sensor has increased fluorescence collection efficiencies from a planar surface and functions effectively using inexpensive photodiodes.

The present invention uses an excitation source to excite fluorescence in the evanescent field of a planar optical waveguide. A photodetectors positioned such that the field of view of the instrument is normal to the waveguide, detects the fluorescence. The sensor uses low-cost photodiodes for detection, permits realistic chemical sensors to be made from thin-layer evanescently excited fluorophores and reduces effective device lengths required in fluorescence detection.

A fluorescence sensor for chemical analysis includes a substrate, a waveguide positioned on the substrate and a chemically sensitive fluorophore film positioned over the waveguide. An excitation source positioned near the waveguide delivers energy to an end facet of the waveguide. A photodetector is placed proximate to the waveguide. The photodetector is positioned such that the field of view of the instrument is normal to the waveguide. A wavelength-selective material film coats a surface of the photodetector. The coating allows fluorescence to be detected and restricts light at an excitation wavelength from reaching the photodetector. The photodetector is positioned a short distance from the waveguide. In one embodiment, the photodetector is located in a hollow portion of the substrate below an active region of the waveguide.

The excitation source is located near the waveguide or connected to the waveguide from a remote location by optical fibers. A prism coupler on an end of the waveguide receives the energy and directs the energy from the excitation source to the waveguide. Alternately, a light emitting diode or a laser diode, is integrated with the waveguide.

The substrate is preferably a glass or polymer substrate. The photodetector is preferably a silicon photodiode having high-aspect ratio (length/width) and a wavelength-selective interference filter. In one embodiment, the waveguide is glass disk treated by potassium-ion exchange. A silver film is applied to outer edges of the disk to provide internal reflection of the energy beam. In a second embodiment, two closely spaced channel waveguides form segments of a composite waveguide. The first segment and the second segment are spaced and lay generally parallel, creating a flow channel between the segments. The lower surface of each segment is connected to the substrate. The upper surface of each segment is brazed or solder connected to the photodetector.

For detection at remote locations, a collector, such as an optical lightguide, is positioned near the waveguide for collecting fluorescence generated by the fluorophores in the waveguide. The collector is connected to a remote photodetector by an optical fiber. In multiplexed sensors having multiple waveguides, a multiple pronged optical lightguide is used, with each prong positioned near a single waveguide for collecting fluorescence generated by the single waveguide. Where the waveguide is segmented, the collector is an optical fiber array positioned near the channel for collecting fluorescence generated by the waveguide.

The method for fluorescence analysis using evanescent wave excitation and out-of-plane photodetection involves preparing a waveguide on a substrate and introducing energy to an end of the waveguide. Energy is introduced directly by coupling the excitation source to the waveguide or indirectly through a prism positioned on an end of the waveguide. The energy produces fluorescence in a chemically-sensitive fluorophore bound to an evanescent region of the waveguide. The fluorescence is detected using a photodetector having a field of view normal to the waveguide. For precise and accurate detection, the photodetector allows fluorescence to pass but restricts light at an excitation wavelength from reaching the photodetector. For detection at remote locations, the fluorescence is collected by a collector and transmitted through an optical fiber to a remote photodetector.

The present invention can be incorporated in automobiles, airplanes and agricultural equipment. The sensors are useful in chemical process control and in environmental applications. The present invention, when employed by automobile manufacturers, provides for precise and inexpensive emissions monitoring and hydrogen vapor monitoring. Firms engaged in distributed chemical analysis can use the present invention with existing chemically sensitive instruments to obtain accurate chemical analysis.

These and further and other objects and features of the invention are apparent in the disclosure, which includes the above and ongoing written specification, with the claims and the drawings.

BRIEF DESCRIPTION OF THE DRAWINGS

FIG. 1 is a schematic illustration of a fluorescent sensor having a substrate, a waveguide positioned on the substrate, a prism coupler, a chemically sensitive fluorophore film positioned on the waveguide, and a photodetector proximate to the waveguide for detecting fluorescence escaping the waveguide.

FIG. 2 is a schematic side illustration of an optical fluorescence sensor showing removal of substrate material to allow positioning of the photodetector close to the waveguide.

FIG. 3 schematically shows an optical lightguide positioned near a waveguide for collecting fluorescence and delivering the fluorescence to a remote photodetector.

FIG. 4 schematically shows a multiplexed fluorescence sensor having multiple waveguides and a multiple pronged lightguide for collecting fluorescence and for delivering the fluorescence to a photodetector array.

DETAILED DESCRIPTION OF THE PREFERRED EMBODIMENTS

Figure 5:
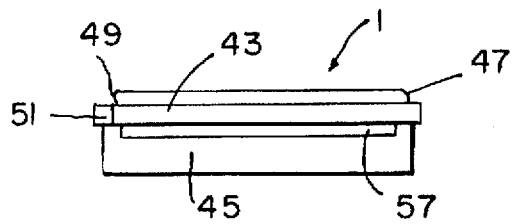
FIG. 5 schematically shows a fluorescence sensor having a glass disk optical waveguide.

Referring to FIGS. 1–8, a fluorescence sensor 1 uses evanescent wave excitation and out-of-plane photodetection to provide precise, sensitive and inexpensive chemical analysis. As shown in FIGS. 1 and 2, a planar optical waveguide 3 is positioned on a substrate 5. A chemically sensitive fluorophore film 7 is deposited over the top surface 9 of the waveguide 3. Energy from an excitation source 11 is directed to an end 13 of the optical waveguide 3. As shown in FIG. 1, one embodiment of the present invention uses a prism coupler 15 positioned on an end 13 of the waveguide 3 to direct the energy onto the waveguide 3. The energy produces fluorescence in the chemically sensitive fluorophore film 7 bound to the evanescent region of the waveguide 3. A photodetector 17 detects the fluorescence generated.

FIGS. 1 and 2 show one embodiment of the present invention wherein the photodetector 17 is closely coupled to the waveguide 3. The substrate 5 has a hollow portion 19 below the active region of the waveguide 3. The waveguide is comprised or two or more dielectric layers which may be deposited on a substrate 5 or on a buffer layer over the photodetector 17. A region of the waveguide may be overlaid by a third dielectric having higher refractive index than the guiding layer of the waveguide to increase interaction with the fluorescent source. A photodetector 17, such as a silicon photodiode, is positioned in the hollow portion 19 of the substrate 5. The proximity of the photodetector 17 to the fluorescence source allows a large fraction of the fluorescence to be captured by the photodetector 17. Preferably, the photodetector 17 is positioned such that the field of view of the instrument is normal to the waveguide 3.

In preferred embodiments, the photodetector surface is coated by a wavelength-selective material that allows fluorescence to be detected but restricts light at the excitation wavelength from reaching the photodetector 17.

FIGS. 3 and 4 show preferred embodiments of the present invention having photodetectors 27 positioned at remote locations. An optical waveguide 29 is situated on a substrate 31 or on the surface of the lightguide 33. The waveguide 29 can be a dye doped polymer waveguide carrying fluorophores. Excitation energy or light is delivered to an end of the waveguide 29, generating fluorescence. A collector 33, such as a lightpipe or lightguide, is positioned in the vicinity of the waveguide 29. The collector 33 allows a considerable portion of fluorescence generated by the excited fluorophore to be brought into the plane of the waveguide 29 for collection and transmission. Optical fiber 35 extends between the collector 33 and the remote photodetector 27 and carries the fluorescence to the photodetector 27.

FIG. 4 shows a multiplexed fluorimeter having multiple waveguides 29 and a multiple pronged collector 33. Light is introduced to a common end 37 of the waveguides 29. The fluorescence generated in each waveguide 29 is collected by a corresponding prong of the collector 33. The collector 33, via optical fibers 35, delivers the fluorescence generated by each waveguide 29 to a remote photodetector array 39. This embodiment is particularly useful for solvent identification.

Figure 6:
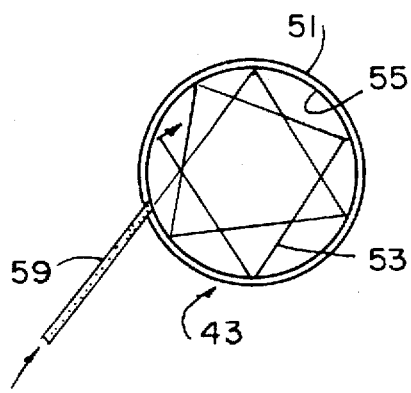
FIG. 6 illustrates how the glass disk optical waveguide of FIG. 5 operates as an optical resonator as the excitation beam reflects inward off side edges of the disk.

FIG. 5 shows one embodiment of the present invention having a disk-shaped waveguide 43. The waveguide 43 is a glass disk that is treated by potassium-ion exchange to prepare an optical waveguide on the surface. The waveguide 43 is positioned on a substrate 45, such as a glass substrate. A chemically sensitive fluorophore film 47 is applied to the upper surface 49 of the waveguide 43. Preferably, the edges 51 of the disk waveguide 43 are silvered such that light propagating in the waveguide 43 undergoes multiple reflections. FIG. 6 shows the path of a light beam 53 as the beam 53 is reflected off the walls 55 of the disk waveguide 43. Multiple internal reflection of the excitation light beams 53 leads to efficient energy transfer to the fluorophore film 47 located in the evanescent field of the waveguide 43.

A photodetector 57, such as a photodiode, detects the fluorescence. FIG. 5 shows a preferred embodiment wherein the photodetector 57 is positioned in the substrate 45 directly beneath the disk waveguide 45. In an alternative embodiment, a collector, such as an optical lightguide, in proximity to the waveguide 43 collects the fluorescence and transmits the fluorescence via an optical fiber located in the plane of the waveguide 43. Light can be directly introduced to the waveguide 43 by an optical fiber 59.

In all embodiments of the present invention, the waveguide 43 is positioned on a substrate 45. Preferably, the optical waveguide 43 is prepared by laser ablation, sol-gel deposition, polymer-solvent deposition or any other coating process. By depositing a waveguide 43 having a thickness equal to or greater than 50 microns, excitation sources, such as laser diodes and light-emitting diodes, can be directly coupled to an end of the waveguide 43.

Figure 7:
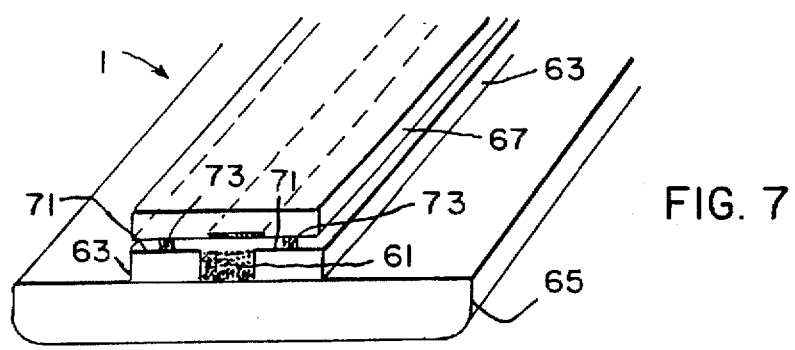
FIG. 7 is a schematic illustration of a microflow-injection fluorescence sensor having a double ridge waveguide, a flow channel between the ridges of the waveguide and a photodetector positioned above the flow channel.
Figure 8:
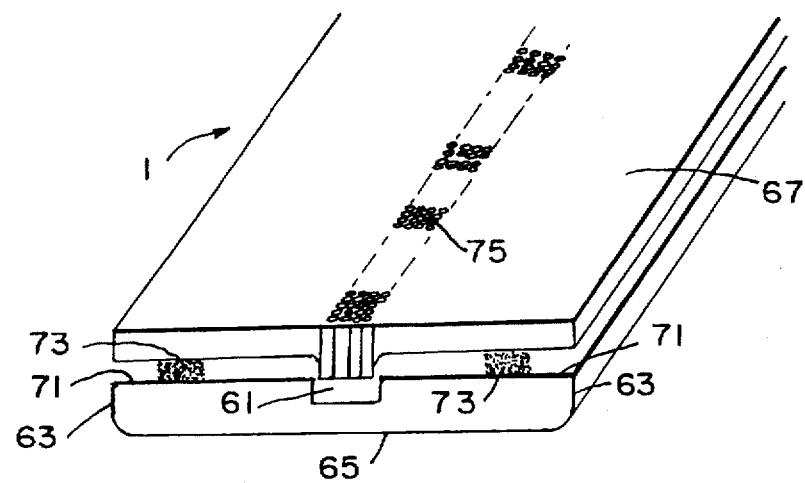
FIG. 8 is a schematic illustration of a microflow-injection fluorescence sensor having a double ridge waveguide, a flow channel between the ridges of the waveguide and an optical fiber array positioned above the flow channel for collecting fluorescence and for delivering the fluorescence to remote photodetectors.

FIGS. 7 and 8 show microflow-injection system embodiments of the present invention. Fluorescence is generated in a flow channel 61 formed as the space between two ridge waveguides 63. The segmented waveguides 63 are positioned on a substrate 65. A high aspect ratio photodetector 67 extends over the channel 61 and is connected to upper surfaces 71 of the waveguide segments 63. In preferred embodiments, the waveguide segments 63 and the photodetector 67 are connected by adhesive joints 73 or brazement. Preferably, the photodetector 67 is positioned such that the field of view of the instrument is normal to the upper surfaces 71 of the waveguide segments 63. The embodiments shown in FIGS. 7 and 8 are advantageous in coupling fluorescence generated by an optical waveguide 63 integrated with a light emitting diode or laser diode to a photodetector 67 for monitoring fluorescence associated with chemical changes. The use of high aspect ratio wavelength-selective photodetectors greatly enhances the collection of fluorescence generated in the evanescent field of an optical fiber. FIG. 7 shows one embodiment of the present invention incorporating a silicon photodetector 67 having high aspect ratio and a wavelength-selective interference filter. FIG. 8 shows another embodiment wherein the photodetector 67 includes an optical fiber array 75 positioned above the flow channel 61.

While the invention has been described with reference to specific embodiments, modifications and variations of the invention may be constructed without departing from the scope of the invention, which is defined in the following claims.

We claim:

1. A sensor apparatus for detecting fluorescence comprising a substrate, a waveguide comprising two or more dielectric layers positioned on the substrate, a chemically sensitive fluorophore film positioned over the waveguide, an excitation source positioned near the waveguide for delivering energy to an end facet of the waveguide, and a photodetector placed proximate to the waveguide and positioned such that a field of view of the photodetector is normal to the waveguide wherein the substrate has a hollow portion below an active region of the waveguide, and wherein the photodetector is positioned in the hollow portion of the substrate.

2. The apparatus of claim 1, further comprising a wavelength-selective material coating positioned over a surface of the photodetector that allows fluorescence to be detected and restricts light at an excitation wavelength from reaching the photodetector.

3. The apparatus of claim 1, further comprising a prism coupler positioned on an end of the waveguide for directing energy from the excitation source to the waveguide.

4. The apparatus of claim 1, wherein the substrate is a glass substrate and the photodetector is a silicon photodiode.

5. The apparatus of claim 1, wherein the waveguide further comprises a glass disk treated by potassium-ion exchange and a silver film applied to outer edges of the disk.

6. The apparatus of claim 5, wherein the substrate is a glass substrate and the photodetector is a silicon photodiode.

7. The apparatus of claim 1, further comprising an optical fiber connected to the excitation source and to the waveguide for integrating the excitation source to the waveguide, and wherein the waveguide contains a section overlaid by high refractive index material to enhance interaction with the fluorophore.

8. A sensor apparatus for detecting fluorescence comprising a substrate, a waveguide comprising two or more dielectric layers positioned on the substrate, a chemically sensitive fluorophore film positioned over the waveguide, an excitation source positioned near the waveguide for delivering energy to an end facet of the waveguide, and a photodetector placed proximate to the waveguide and positioned such that a field of view of the photodetector is normal to the waveguide, wherein the waveguide has a first segment and a second segment lying generally parallel to the first segment, thereby creating a channel between the segments of the waveguide.

9. The apparatus of claim 8, wherein each waveguide segment has an upper surface and a lower surface, the lower surface connected to the substrate, and wherein the photodetector is connected to the upper surfaces of the waveguide segments.

10. The apparatus of claim 9, wherein the photodetector and the segments of the waveguide are connected by adhesive joints.

11. The apparatus of claim 9, wherein the photodetector comprises a silicon photodiode having high-aspect ratio and a wavelength-selective interference filter.

12. The apparatus of claim 11, wherein the waveguide is a polymer waveguide, wherein the substrate is a glass substrate.

13. The apparatus of claim 9, wherein the excitation source is selected from a group consisting of a light emitting diode and a laser diode, and wherein the excitation source is integrated with the waveguide.

14. The apparatus of claim 1 wherein the waveguide has a thickness of at least 50 microns.

15. A sensor apparatus for detection at remote locations comprising a substrate, at least one waveguide positioned on the substrate, the waveguide carrying fluorophores, an excitation source positioned near the waveguide for delivering energy to an end of the waveguide, a collector positioned near the waveguide for collecting fluorescence generated by the fluorophores in the waveguide, a remote photodetector and an optical fiber connected to the photodetector and to the collector, wherein the collector is an optical lightguide, and wherein multiple waveguides are positioned on the substrate, and wherein the lightguide has multiple prongs, with each prong positioned near a single waveguide for collecting fluorescence generated by the single waveguide.

16. A sensor apparatus for detection at remote locations comprising a substrate, at least one waveguide positioned on the substrate, the waveguide carrying fluorophores, an excitation source positioned near the waveguide for delivering energy to an end of the waveguide, a collector positioned near the waveguide for collecting fluorescence generated by the fluorophores in the waveguide, a remote photodetector and an optical fiber connected to the photodetector and to the collector, wherein the waveguide is a dye doped polymer waveguide, deposited on the surface of the collector.

17. A sensor apparatus for detection at remote locations comprising a substrate, at least one waveguide positioned on the substrate, the waveguide carrying fluorophores, an excitation source positioned near the waveguide for delivering energy to an end of the waveguide, a collector positioned near the waveguide for collecting fluorescence generated by the fluorophores in the waveguide, a remote photodetector and an optical fiber connected to the photodetector and to the collector, wherein the waveguide has a first segment and a second segment lying generally parallel to the first segment, thereby creating a channel between the segments of the waveguide, and wherein the collector is an optical fiber array positioned near the channel for collecting fluorescence generated by the waveguide.

18. The apparatus of claim 1, wherein the waveguide is comprised of at least two or more dielectric layers, and wherein the excitation source is directly coupled to the waveguide, and wherein the waveguide is deposited on a low-refractive index buffer layer, deposited on the photodetector.

* * * * *